(12) United States Patent
Tanner et al.

(10) Patent No.: US 9,074,249 B2
(45) Date of Patent: Jul. 7, 2015

(54) DETECTION OF AMPLIFICATION PRODUCTS

(71) Applicant: New England Biolabs, Inc., Ipswich, MA (US)

(72) Inventors: Nathan Tanner, Peabody, MA (US); Yinhua Zhang, North Reading, MA (US); Thomas C. Evans, Topsfield, MA (US)

(73) Assignee: New England Biolabs, Inc., Ipswich, MA (US)

( * ) Notice: Subject to any disclaimer, the term of this patent is extended or adjusted under 35 U.S.C. 154(b) by 76 days.

(21) Appl. No.: 13/834,919

(22) Filed: Mar. 15, 2013

(65) Prior Publication Data

US 2013/0323738 A1    Dec. 5, 2013

Related U.S. Application Data

(60) Provisional application No. 61/655,033, filed on Jun. 4, 2012, provisional application No. 61/676,730, filed on Jul. 27, 2012, provisional application No. 61/692,500, filed on Aug. 23, 2012, provisional application No. 61/722,830, filed on Nov. 6, 2012.

(51) Int. Cl.
*C12P 19/34* (2006.01)
*C12Q 1/68* (2006.01)

(52) U.S. Cl.
CPC .................................... *C12Q 1/6853* (2013.01)

(58) Field of Classification Search
CPC ........... C12Q 1/6853; C12Q 2527/143; C12Q 2537/161; C12Q 2565/101; C12Q 2525/301; C12Q 2531/119
USPC ........................................................ 435/91.2
See application file for complete search history.

(56) References Cited

U.S. PATENT DOCUMENTS

| 6,270,967 | B1 | 8/2001 | Whitcombe et al. | |
|---|---|---|---|---|
| 8,076,067 | B2 | 12/2011 | Shafer | |
| 2008/0160524 | A1* | 7/2008 | Ma et al. | 435/6 |
| 2009/0068643 | A1 | 3/2009 | Behlke et al. | |
| 2010/0055685 | A1 | 3/2010 | Saul | |
| 2011/0008787 | A1 | 1/2011 | Satterfield et al. | |
| 2011/0207131 | A1 | 8/2011 | Fu | |

FOREIGN PATENT DOCUMENTS

| WO | WO2008/063194 A1 | 5/2008 |
|---|---|---|
| WO | WO2009/079215 A1 | 6/2009 |
| WO | WO2009108693 A2 | 9/2009 |
| WO | WO2010013017 A1 | 2/2010 |
| WO | WO2011055875 A1 | 5/2011 |
| WO | WO2011078441 A1 | 6/2011 |
| WO | WO2011010057 A2 | 8/2011 |
| WO | WO2011142836 A2 | 11/2011 |
| WO | WO2011163425 A1 | 12/2011 |
| WO | WO2012024642 A1 | 2/2012 |
| WO | WO2012154876 A1 | 11/2012 |

OTHER PUBLICATIONS

Notomi, et al., Nucleic Acids Research, 28:E63 (2000).
Gill, et al., Nucleosides, Nucleotides and Nucleic Acids, 27:224-243 (2008).
Nagamine, et al., Mol. Cell. Probes, 16:223-229 (2002).
Kim, et al., Bioanalysis, 3:227-39 (2011).
Niemz, et al., Trends Biotechnol, 29:240-50 (2011).
Nagamine, et al., Clin Chem, 47:1742-3 (2001).
Goto, et al., Biotechniques, 46: 167-72 (2009).
Ganddelman, et al., PLoS One 5:e14155 (2010).
Mori, et al., Biochem Biophys Methods, 59:145-57 (2004).
Mori, et al., Biochem Biophys res Commun, 289:150-4 (2001).
Tomita, et al., Nat Protoc, 3:877-82 (2008).
Tao, et al., Parasit Vectors, 4:115 (2011).
Holland, et al., Proc Natl Acad Sci, USA, 88:7276-80 (1991).
Vanguilder, Biotechniques, 44:619-26 (2008).
Didenko, Biotechniques, 31:1106-16, 118, 1120-1 (2001).
Bustin, A-Z of Quantitative PCR, International University Line, La Jolla, CA (2006).
Aonuma, et al., Exp Parasitol, 125:179-83 (2010).
He, et al., Aquaculture, 311:94-99 (2010).
Liang, et al., Anal Chem, 84:3758-63 (2012).
Zerilli, et al., Clim Chem, 56:1287-96 (2010).
Kouguchi, et al., Mol Cell Probes, 24:190-5 (2010).
Kimura, et al., Nucleic Acids Research, 39:e59 (2011).
Gandelman, et al., Int. J. Mol. Sci, 12:9108-9124 (2011).
Whitecombe, et al., Nature Biotechnology, 17:804-807 (1999).
Yi, et al., Nucleic Acids Reserach, 34, 11:e81 (2006).
International Search Report for PCT/US2013/052189—International filing date Jul. 26, 2013.
Mori, J Infect Chemother, 15, 62-69, 2009.
Cai, et al., Jounral of Clinical Virology, 41, 270-276, 2008.
Chou, et al, Journal of Virological Methods, 173, 67-74, 2011.
Miyamoto, Amplicon Engineering for Improved Bacterial Detection Using LAMP May 9, 2010.
Tanner, et al, BioTechniques, 53, 81-89, 2012.

* cited by examiner

*Primary Examiner* — Cynthia B Wilder
(74) *Attorney, Agent, or Firm* — New England Biolabs, Inc; Harriet M. Strimpel

(57) ABSTRACT

Compositions and methods are provided for quantitative detection of amplification products, the methods being suitable for multiplexing. A first oligonucleotide that includes a primer sequence for priming an amplification reaction and also is labeled with a fluorescent label or quencher is mixed with a second oligonucleotide which has a sequence suitable for hybridizing to a portion of the first oligonucleotide and has a fluorescent label if the first oligonucleotide has a quencher or a quencher if the first oligonucleotide has a fluorescent label; and a third nucleotide which includes some or all the primer sequence contained in the first oligonucleotide but is not labeled, the first and third oligonucleotide being combined in a molar ratio of 2.8 to 8.2.

14 Claims, 8 Drawing Sheets

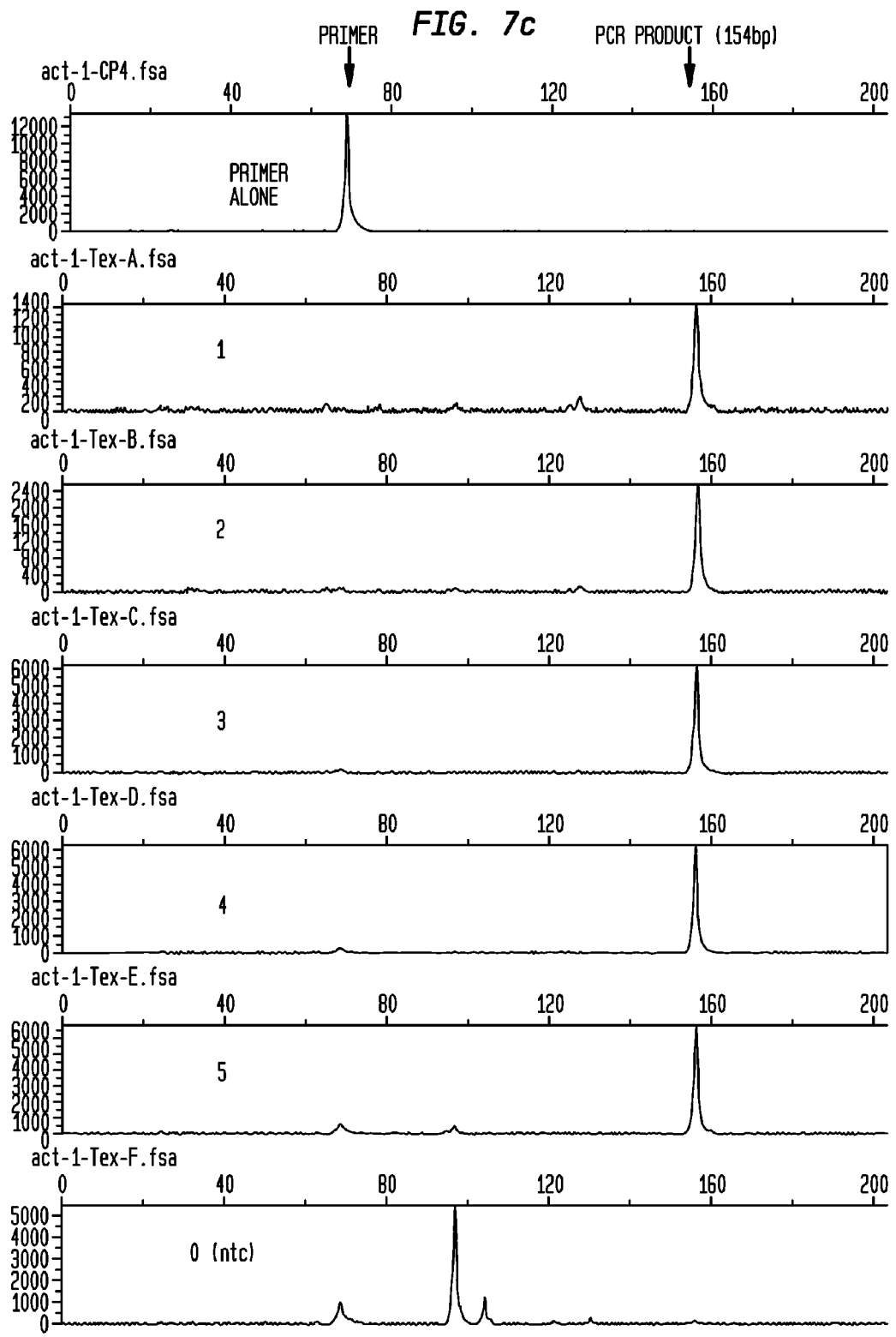

SEQUENCE LISTING

<160> NUMBER OF SEQ ID NOS: 48

<210> SEQ ID NO 1
<211> LENGTH: 45
<212> TYPE: DNA
<213> ORGANISM: Escherichia coli

<400> SEQUENCE: 1
ctgccccgac gataggctta atcgtggtct ggtgaagttc tacgg        45

<210> SEQ ID NO 2
<211> LENGTH: 22
<212> TYPE: DNA
<213> ORGANISM: Escherichia coli

<400> SEQUENCE: 2
attaagccta tcgtcggggc ag        22

<210> SEQ ID NO 3
<211> LENGTH: 45
<212> TYPE: DNA
<213> ORGANISM: Escherichia coli

<400> SEQUENCE: 3
ctgccccgac gataggctta atcgtggtct ggtgaagttc tacgg        45

<210> SEQ ID NO 4
<211> LENGTH: 42
<212> TYPE: DNA
<213> ORGANISM: Escherichia coli

<400> SEQUENCE: 4
tccagtgcga cctgctgggt gggtattgtt cgccgccagt ac        42

<210> SEQ ID NO 5
<211> LENGTH: 20
<212> TYPE: DNA
<213> ORGANISM: Escherichia coli

<400> SEQUENCE: 5
gatcaccgat ttcaccaacc        20

<210> SEQ ID NO 6
<211> LENGTH: 22
<212> TYPE: DNA
<213> ORGANISM: Escherichia coli

<400> SEQUENCE: 6
cttttgagat cagcaacgtc ag        22

<210> SEQ ID NO 7
<211> LENGTH: 16
<212> TYPE: DNA
<213> ORGANISM: Escherichia coli

<400> SEQUENCE: 7
tgcgccatgt cccgct        16

<210> SEQ ID NO 8
<211> LENGTH: 19
<212> TYPE: DNA
<213> ORGANISM: Escherichia coli

<400> SEQUENCE: 8

```
tgagttaacc cacctgacg                                              19
```

<210> SEQ ID NO 9
<211> LENGTH: 46
<212> TYPE: DNA
<213> ORGANISM: enterobacteria phage lambda

<400> SEQUENCE: 9

```
cagccagccg cagcacgttc gctcatagga gatatggtag agccgc                46
```

<210> SEQ ID NO 10
<211> LENGTH: 21
<212> TYPE: DNA
<213> ORGANISM: enterobacteria phage lambda

<400> SEQUENCE: 10

```
cgaacgtgct gcggctggct g                                           21
```

<210> SEQ ID NO 11
<211> LENGTH: 46
<212> TYPE: DNA
<213> ORGANISM: enterobacteria phage lambda

<400> SEQUENCE: 11

```
cagccagccg cagcacgttc gctcatagga gatatggtag agccgc                46
```

<210> SEQ ID NO 12
<211> LENGTH: 51
<212> TYPE: DNA
<213> ORGANISM: enterobacteria phage lambda

<400> SEQUENCE: 12

```
gagagaattt gtaccacctc ccaccgggca catagcagtc ctagggacag t          51
```

<210> SEQ ID NO 13
<211> LENGTH: 22
<212> TYPE: DNA
<213> ORGANISM: enterobacteria phage lambda

<400> SEQUENCE: 13

```
ggcttggctc tgctaacacg tt                                          22
```

<210> SEQ ID NO 14
<211> LENGTH: 22
<212> TYPE: DNA
<213> ORGANISM: enterobacteria phage lambda

<400> SEQUENCE: 14

```
ggacgtttgt aatgtccgct cc                                          22
```

<210> SEQ ID NO 15
<211> LENGTH: 17
<212> TYPE: DNA
<213> ORGANISM: enterobacteria phage lambda

<400> SEQUENCE: 15

```
ctgcatacga cgtgtct                                                17
```

<210> SEQ ID NO 16
<211> LENGTH: 20
<212> TYPE: DNA
<213> ORGANISM: enterobacteria phage lambda

```
<400> SEQUENCE: 16
accatctatg actgtacgcc                                            20

<210> SEQ ID NO 17
<211> LENGTH: 44
<212> TYPE: DNA
<213> ORGANISM: Caenorhabditis elegans

<400> SEQUENCE: 17
gattccactt ccaacgtcgt tgcataggca ttgtatccag agtg                 44

<210> SEQ ID NO 18
<211> LENGTH: 22
<212> TYPE: DNA
<213> ORGANISM: Caenorhabditis elegans

<400> SEQUENCE: 18
caacgacgtt ggaagtggaa tc                                         22

<210> SEQ ID NO 19
<211> LENGTH: 44
<212> TYPE: DNA
<213> ORGANISM: Caenorhabditis elegans

<400> SEQUENCE: 19
gattccactt ccaacgtcgt tgcataggca ttgtatccag agtg                 44

<210> SEQ ID NO 20
<211> LENGTH: 42
<212> TYPE: DNA
<213> ORGANISM: Caenorhabditis elegans

<400> SEQUENCE: 20
cgaagtgaac cttgtcaaca tgagactacc cacatcgtta cc                   42

<210> SEQ ID NO 21
<211> LENGTH: 20
<212> TYPE: DNA
<213> ORGANISM: Caenorhabditis elegans

<400> SEQUENCE: 21
agcaacatag gtttcagttc                                            20

<210> SEQ ID NO 22
<211> LENGTH: 18
<212> TYPE: DNA
<213> ORGANISM: Caenorhabditis elegans

<400> SEQUENCE: 22
ctgtgaacgg tcatcacc                                              18

<210> SEQ ID NO 23
<211> LENGTH: 20
<212> TYPE: DNA
<213> ORGANISM: Caenorhabditis elegans

<400> SEQUENCE: 23
acggacatgt cgatcatgga                                            20

<210> SEQ ID NO 24
<211> LENGTH: 22
<212> TYPE: DNA
<213> ORGANISM: Caenorhabditis elegans
```

```
<400> SEQUENCE: 24
cgtctccctt caatccgatg gc                                              22

<210> SEQ ID NO 25
<211> LENGTH: 48
<212> TYPE: DNA
<213> ORGANISM: Homo sapiens

<400> SEQUENCE: 25
ccaaagagta aagtccttct ctctcgagag actgttggcc cttgaagg                  48

<210> SEQ ID NO 26
<211> LENGTH: 22
<212> TYPE: DNA
<213> ORGANISM: Homo sapiens

<400> SEQUENCE: 26
agagagaagg actttactct tt                                              22

<210> SEQ ID NO 27
<211> LENGTH: 48
<212> TYPE: DNA
<213> ORGANISM: Homo sapiens

<400> SEQUENCE: 27
ccaaagagta aagtccttct ctctcgagag actgttggcc cttgaagg                  48

<210> SEQ ID NO 28
<211> LENGTH: 47
<212> TYPE: DNA
<213> ORGANISM: Homo sapiens

<400> SEQUENCE: 28
gtgttgatgt tatccacctt ttgtggacta ggaaaacaga tcaatag                   47

<210> SEQ ID NO 29
<211> LENGTH: 20
<212> TYPE: DNA
<213> ORGANISM: Homo sapiens

<400> SEQUENCE: 29
taatcctgga actccggtgc                                                 20

<210> SEQ ID NO 30
<211> LENGTH: 23
<212> TYPE: DNA
<213> ORGANISM: Homo sapiens

<400> SEQUENCE: 30
tttatgccaa ttaacatttt gac                                             23

<210> SEQ ID NO 31
<211> LENGTH: 19
<212> TYPE: DNA
<213> ORGANISM: Homo sapiens

<400> SEQUENCE: 31
atccacaggg aggagctct                                                  19

<210> SEQ ID NO 32
<211> LENGTH: 19
<212> TYPE: DNA
```

```
<213> ORGANISM: Homo sapiens

<400> SEQUENCE: 32
ctccacctat aaaatcggc                                                     19

<210> SEQ ID NO 33
<211> LENGTH: 45
<212> TYPE: DNA
<213> ORGANISM: Homo sapiens

<400> SEQUENCE: 33
atccccagtc tgtgaaattg ggcaaaatgc tgggattata gatgt                        45

<210> SEQ ID NO 34
<211> LENGTH: 21
<212> TYPE: DNA
<213> ORGANISM: Homo sapiens

<400> SEQUENCE: 34
ccaatttcac agactgggga t                                                  21

<210> SEQ ID NO 35
<211> LENGTH: 45
<212> TYPE: DNA
<213> ORGANISM: Homo sapiens

<400> SEQUENCE: 35
atccccagtc tgtgaaattg ggcaaaatgc tgggattata gatgt                        45

<210> SEQ ID NO 36
<211> LENGTH: 47
<212> TYPE: DNA
<213> ORGANISM: Homo sapiens

<400> SEQUENCE: 36
gcagcagaaa gattattaac ttgggcagtt ggtaagtaaa tggaaga                      47

<210> SEQ ID NO 37
<211> LENGTH: 19
<212> TYPE: DNA
<213> ORGANISM: Homo sapiens

<400> SEQUENCE: 37
tccttgaact ttggtctcc                                                     19

<210> SEQ ID NO 38
<211> LENGTH: 23
<212> TYPE: DNA
<213> ORGANISM: Homo sapiens

<400> SEQUENCE: 38
cagttcataa aggaattgat agc                                                23

<210> SEQ ID NO 39
<211> LENGTH: 20
<212> TYPE: DNA
<213> ORGANISM: Homo sapiens

<400> SEQUENCE: 39
agaaccagag gccaggcgag                                                    20

<210> SEQ ID NO 40
<211> LENGTH: 22
```

```
<212> TYPE: DNA
<213> ORGANISM: Homo sapiens

<400> SEQUENCE: 40
aggcagatag gcttagactc aa                                              22

<210> SEQ ID NO 41
<211> LENGTH: 65
<212> TYPE: DNA
<213> ORGANISM: Escherichia coli

<400> SEQUENCE: 41
ccgcgtgtat gaagaaggcc ttcgggttgt aaagtacttt cagcggggag gaagggagta    60
aagtt                                                                 65

<210> SEQ ID NO 42
<211> LENGTH: 41
<212> TYPE: DNA
<213> ORGANISM: Escherichia coli

<400> SEQUENCE: 42
gaaagtactt tacaacccga aggccttctt catacacgcg g                         41

<210> SEQ ID NO 43
<211> LENGTH: 24
<212> TYPE: DNA
<213> ORGANISM: Escherichia coli

<400> SEQUENCE: 43
agcggggagg aagggagtaa agtt                                            24

<210> SEQ ID NO 44
<211> LENGTH: 25
<212> TYPE: DNA
<213> ORGANISM: Escherichia coli

<400> SEQUENCE: 44
cagtatcaga tgcagttccc aggtt                                           25

<210> SEQ ID NO 45
<211> LENGTH: 65
<212> TYPE: DNA
<213> ORGANISM: Caenorhabditis elegans

<400> SEQUENCE: 45
aggatatgcc ctcccacacg ccatcctccg tcttgacttg gctggacgtg atcttactga    60
ttacc                                                                 65

<210> SEQ ID NO 46
<211> LENGTH: 40
<212> TYPE: DNA
<213> ORGANISM: Caenorhabditis elegans

<400> SEQUENCE: 46
caagtcaaga cggaggatgg cgtgtgggag ggcatatcct                           40

<210> SEQ ID NO 47
<211> LENGTH: 25
<212> TYPE: DNA
<213> ORGANISM: Caenorhabditis elegans

<400> SEQUENCE: 47
```

```
gctggacgtg atcttactga ttacc                                      25

<210> SEQ ID NO 48
<211> LENGTH: 24
<212> TYPE: DNA
<213> ORGANISM: Caenorhabditis elegans

<400> SEQUENCE: 48
gtagcagagc ttctccttga tgtc                                       24
```

US 9,074,249 B2

DETECTION OF AMPLIFICATION PRODUCTS

REFERENCE TO RELATED APPLICATIONS

This application claims the benefit of each of the following patent applications, the entire disclosures of each of which are hereby incorporated by reference into the present application: U.S. 61/676,730, filed Jul. 27, 2012; U.S. 61/655,033, filed Jun. 4, 2012; U.S. 61/692,500, filed Aug. 23, 2012; U.S. 61/722,830, filed Nov. 6, 2012; U.S. Ser. No. 13/799,463, filed Mar. 13, 2013; and U.S. Ser. No. 13/799,995, filed Mar. 13, 2013.

BACKGROUND

Sequence-specific isothermal and polymerase chain reaction (PCR) nucleic acid amplification techniques represent a rapidly growing sector of molecular diagnostics, offering rapid, sensitive detection of DNA samples.

Several isothermal techniques require multiple enzymes to work in concert, for example, strand displacement amplification (SDA), helicase dependent amplification (HDA), and isothermal and chimeric primer-initiated amplification of nucleic acids (ICAN). Loop mediated isothermal amplification (LAMP) provides sequence-specific amplification using only a strand-displacing DNA polymerase (Gill and Ghaemi, *Nucleosides, Nucleotides, and Nucleic Acids*, 27:224-43 (2008); Kim and Easley, *Bioanalysis*, 3:227-39 (2011)). In addition to the DNA polymerase, LAMP uses 4 core primers (FIP, BIP, F3, and B3) recognizing 6 distinct sequence regions on the target (FIG. 1(a)-(b)), with two primers containing sequence (F1C, B1C) that results in loop structures which facilitate exponential amplification (Notomi, et al., *Nucleic Acids Res.*, 28:E63 (2000)). The use of multiple target sequence regions confers a high degree of specificity to the reaction. Two additional primers, termed loop primers, can be added to increase reaction speed, resulting in 6 total primers used per target sequence (Nagamine, et al., *Mol. Cel. Probes*, 16:223-9 (2002)). The LAMP reaction rapidly generates amplification products as multimers of the target region in various sizes, and is substantial in total DNA synthesis (>10 µg, >50×PCR yield) (Notomi, et al. (2000); Nagamine, et al., *Clin. Chem.*, 47:1742-3 (2001)) (see FIG. 1(a)-(b)).

Measurement of LAMP amplification product may be performed using fluorescence detection of double-stranded DNA (dsDNA) with an intercalating or magnesium-sensitive fluorophore (Notomi, et al. (2000); Goto, et al., *Biotechniques*, 46:167-72, (2009)), bioluminescence through pyrophosphate conversion (Gandelman, et al, *PloS One*, 5:e14155 (2010)), turbidity detection of precipitated magnesium pyrophosphate (Mori, et al., *Biochem. Biophys. Methods* 59:145-57 (2004); Mori, et al., *Biochem. Biophys Res. Commun.*, 289:150-4 (2001)), or even visual examination through precipitated $Mg_2P_2O_7$ or metal-sensitive dye (Tomita, *Nat. Protoc.*, 3:877-82 (2008); Tao, et al., *Parasit Vectors*, 4:115 (2011)). These methods are robust and familiar, and visual methods are ideal for use in field diagnostics, but detect total DNA amplification in a reaction and are thus limited to detection of a single target. As isothermal techniques are further adopted as diagnostic tools, the ability to detect multiple targets in a single sample is desirable. Currently, quantitative, real-time PCR (qPCR) enables probe-specific multiplex detection and the ability to perform tests with an internal standard for definitive negative results. However, qPCR probes require extensive design and optimization for use and may not effectively translate to the LAMP reaction (Holland, et al., *Proc Natl Acad Sci USA*, 88:7276-80 (1991); VanGuilder, et al., *Biotechniques* 44:619-26 (2008); Didenko, *Biotechniques* 31:1106-16, 1118, 1120-1 (2001); Bustin, *A-Z of Quantitative PCR*. International University Line, La Jolla, Calif. (2006)).

Samples containing several different DNAs of interest have been analyzed using endpoint agarose gel electrophoresis (Aonuma, et al., *Exp Parasitol*, 125:179-83 (2010); He, et al., *Aquaculture*, 311:94-99 (2010)) or pyrosequencing (Li-ang, et al., *Anal Chem*, 84:3758-63 (2012)) but these do not allow real-time detection and require additional processing and instrumentation. In addition, the sensitivity of LAMP reactions to carryover contamination is so great that manufacturer recommendations (Eiken Chemical, Tokyo, Japan) suggest not opening LAMP reaction vessels, or doing so in separate facilities with separate equipment, further decreasing the desirability of post-LAMP manipulation. Previous real-time methods use non-specific quenching, either through loss-of-signal guanine quenching (Zerilli, et al., *Clin Chem*, 56:1287-96 (2010)) or gain-of-signal fluorescence using labeled primers and an intercalating dye (Kouguchi, et al., *Mol Cell Probes*, 24:190-5 (2010)). These methods can be less sensitive, and nonspecific quenching limits the selection of fluorophores available for multiplexing.

PCR requires a pair of primers and thermophilic DNA polymerase such as Taq DNA polymerase. During amplification, cycles of denaturation, annealing and primer extension steps allow primers to bind to the target sequence and DNA synthesis. Two types of detection are commonly used: endpoint or real time. A typical endpoint detection is agarose gel electrophoresis that allow identification of the specific target based on amplicon size and the yield. Realtime PCR or qPCR monitors the DNA production while the target DNA are being amplified.

The detection of qPCR can be divided into two types: the first type uses a double strand DNA intercalating dye and the second type uses a sequence specific probes. A number of methods have been described using sequence-specific probe (Holland, et al. (1991); VanGuilder, et al. (2008); Didenko (2001); Bustin (2006)). However, these typically require design of fluorescent probes in addition to the PCR primers.

SUMMARY

In general in one aspect, a composition is provided in a buffer, that includes: a first oligonucleotide comprising a primer sequence which is also a target sequence for priming an amplification reaction, the first oligonucleotide having a quencher or fluorescent label; a second oligonucleotide having a sequence suitable for hybridizing to a portion of the first oligonucleotide under stringent conditions to form a stable duplex, the second oligonucleotide having a fluorescent label if the first oligonucleotide has a quencher label, or having a quencher label if the first oligonucleotide has a fluorescent label; and a third oligonucleotide comprising some or all of the primer sequence contained in the first oligonucleotide and not including a quenching or fluorescent label wherein the molar ratio of the first oligonucleotide to the third nucleotide is in the range of 2:8 to 8:2.

Various embodiments of the composition include one or more of the following features: the second oligonucleotide at a concentration that is substantially the same as the first oligonucleotide; the first oligonucleotide having a quencher label and the second oligonucleotide having a fluorescent label or the first oligonucleotide having a fluorescent label and the second oligonucleotide having a quencher label; the first oligonucleotide and the third oligonucleotide combined in at least 1:1 molar ratio; a strand displacement polymerase; and/or a plurality of polymerases, wherein one of the polymerases is an archeal polymerase.

In general, in one aspect, a method for detecting an amplification product of a polynucleotide is provided that includes; adding to a polynucleotide: a first oligonucleotide comprising a primer sequence for priming the amplification from the polynucleotide template at a first location on the polynucleotide and having a quencher or fluorescent label; and a second oligonucleotide hybridized to the first oligonucleotide under stringent conditions to form a stable duplex and having a fluorescent label if the first oligonucleotide has a quencher label, or having a quencher label if the first oligonucleotide has a fluorescent label; and a third oligonucleotide comprising some or all of the primer sequence contained in the first oligonucleotide and not including a quenching or fluorescent label wherein the molar ratio of the first oligonucleotide to the third nucleotide is in the range of 2:8 to 8:2; permitting amplification of the polynucleotide; and detecting the amplified product of the polynucleotide.

Various embodiments of the method include additionally adding one or more of the following features: a strand displacement polymerase; a plurality of polymerases, wherein one of the polymerases is an archeal polymerase; a fourth oligonucleotide comprising some or all of a sequence for annealing to a priming site on a second location on the polynucleotide; and/or a fourth, fifth and sixth oligonucleotide where the fourth oligonucleotide is unlabeled and competes with a dimerized labeled fifth and sixth oligonucleotide; an amount of the first oligonucleotide being X/N where X is the optimal primer concentration in a single-plex reaction and N is the number of different templates for which primer sets are present in the reaction mixture, and/or X is in the range of 0.1 µM-2 µM.

Other features may optionally include one or more of the following: the first oligonucleotide having a quencher label and the second oligonucleotide having a fluorescent label, or the first oligonucleotide having a fluorescent label and the second oligonucleotide having a quencher label; and/or combining the first oligonucleotide and the third oligonucleotide in at least a 1:1 ratio.

Other features may include releasing the second oligonucleotide by means of primer extension from the fourth oligonucleotide.

Additional features may include amplifying DNA using PCR, reverse transcription PCR, LAMP, or reverse transcription LAMP; detecting an amplification product of multiple polynucleotides in a multiplex reaction mixture and optionally including an internal standard; and/or determining the size of the amplification product. Additional features include the monitoring of amplification using pH sensitive dyes described in U.S. patent application Ser. No. 13/799,995. Non-template amplification may be inhibited using the compositions and methods described in U.S. patent application Ser. No. 13/799,463.

BRIEF DESCRIPTION OF THE FIGURES

FIG. 1(a) shows 3 different oligonucleotides (Oligo 1 (labeled F1c-F2), Oligo 2 (labeled F1) and Oligo 3 (unlabeled F1c-F2)) identified as a forward internal primer (FIP) because of the association with one end of the target DNA (3' end). In this Figure, the label is a 5'-quencher (black star) or 3'-fluorophore of F1c (white star). The sequences of Oligo 1, 2 and 3 correspond to the target sequence at the 3' end as shown in FIG. 1(b)(i).

FIG. 1(b)(i-iv) shows LAMP amplification with the three forward oligonucleotides described in FIG. 1(a) and a backward oligonucleotide (Oligo 4) (unlabelled B1c-B2) at the 5' end of the DNA. A labeled Oligo 4 may be used with an Oligo 5/6; (B2-B1c/B1) to further increase the detection signal.

FIG. 1(b)(i) shows initiation of amplification of a polynucleotide template. Polymerase activity initiates from F2 which acts as a single strand primer having a double-stranded labeled tail which has a quenched fluorescent terminus. The strand displacement activity of the DNA polymerase initiates from F3 to "bump" the downstream product from initiation at F2.

FIG. 1(b)(ii) The new displaced strand is replicated from unlabelled Oligo 4 initiation (B2) and displacement via B3.

FIG. 1(b)(iii) Full extension from B2 displaces the fluorescent Oligo 2 annealed to the first strand resulting in a fluorescent signal.

FIG. 1(b)(iv) The newly synthesized strand is displaced from the complementary strand during synthesis and can anneal with itself at the complementary regions of F1-F1c and B1-B1c. Thus Oligo 1 and 2 through F2 can again anneal to F2c and the cycle is repeated giving rise to exponential amplification. (LoopF and LoopB primers are not shown).

FIGS. 2(a) and 2(c) the primer sequence is entirely complementary to the priming region in the target polynucleotide whereas in FIGS. 2(b) and 2(d) the primer is shown to have only partial complementarity with the priming sequence in the target polynucleotide where the F2 primer may extend 3' or 5' beyond the priming sequence as shown.

FIG. 2(a) shows LAMP primers where the primer is complementary to the priming region and where Oligo 3 is the same as oligo 1 but without L1.

FIG. 2(b) shows LAMP primers where the primer is only partially complementary to the priming region and where Oligo 3 is the same as oligo 1 but without L1.

FIG. 2(c) shows PCR primers where the primer is complementary to the priming region and where Oligo 3 corresponds to F2 only.

FIG. 2(d) shows PCR primers where the primer is only partially complementary to the priming region and where Oligo 3 corresponds to F2 only.

FIG. 3(a) shows detection of lambda DNA with HEX-labeled Oligo 1 (dark quencher on Oligo 2) and C. elegans DNA (lec-10) with ROX-labeled Oligo 2 (dark quencher on Oligo 1).

FIG. 3(b) shows detection of E. coli DNA (dnaE) with Cy5-labeled Oligo 2 and human DNA (BRCA1) with Cy5.5-labeled Oligo 2, with dark quencher labeled Oligo 1.

FIG. 3(c) shows maintenance of amplification for a single concentration internal standard (82.5 ng C. elegans genomic DNA; lec-10 target; ROX Oligo 2) that is not influenced by and therefore independent of LAMP amplification of varying amounts of a test target DNA (10 pg-100 ng HeLa genomic DNA; CFTR target; 6-FAM Oligo 2). In this multiplex reaction, the relatively high concentration of the standard is amplified at a high rate while 10 pg of Hela genomic DNA is amplified significantly slower although the amplification rate is increased as expected with increasing concentration of Hela genomic DNA.

FIG. 4(a) shows a triplex reaction that results in detection of three genomic DNAs: E. coli genomic DNA (Cy5 Oligo 2), lambda genomic DNA (HEX Oligo 1), and C. elegans genomic DNA (ROX Oligo 2). Concentration of each primer set was scaled by ⅓ for triplex reactions.

FIG. 4(b) shows the detection of four genomic DNAs where three DNAs are the same as used in the triplex in FIG. 4(a) and the fourth DNA is human genomic DNA (Cy5.5 Oligo 2). The concentration of each primer set was scaled by ¼ for quadruplex reactions. The same overall concentration of primers as in FIG. 4(a) was maintained. Reactions contained eight oligonucleotides per target and thirty-two total oligonucleotides in quadruplex reaction.

FIG. 6(a) shows realtime fluorescence signal during PCR cycling.

FIG. 6(b) shows the resulting standard curve, determined by the cycle number when the signal crossing the amplification threshold (Cq value, Y-axis) plotted against the log value of the copy number.

FIG. 7(a) shows realtime fluorescence signal during PCR cycling.

FIG. 7(b) shows that the Ct value correlated tightly with the copy number of the target gene in the DNA quantification curve.

FIG. 7(c) shows the size value (154 bp) of the product DNA as measured by post-PCR capillary electrophoresis detecting the product-incorporated TEX label. Only reactions containing template DNA resulted in a electropherogram peak, demonstrating the ability to detect specific sizes of product DNA.

DETAILED DESCRIPTION OF EMBODIMENTS

Compositions and methods are provided for gain-of-signal and target-specific detection of amplification products of polynucleotides that are easily implemented, reproducible and sensitive. The gain-of-signal and target specific detection is observed after displacement of a labeled quencher or fluorescent label by polymerase-dependent extension of the polynucleotide containing the target sequence.

Advantages of present embodiments include at least one of the following: (a) increased sensitivity and time frame of a quantitative amplification reaction (b) no additional primer optimization or probe design beyond a 5' labelled primer with a complementary detection oligonucleotide (Oligo 1/2) and unlabeled Oligo 3; (c) availability of an internal quantification standard; (d) ability to perform size detection; (e) applicability to a variety of amplification procedures; and (f) capacity for multiplexing multiple samples limited only by available fluorophors and detectors.

Sets of oligonucleotides have been developed that can be used in multiplex isothermal amplification reactions to detect and optionally quantify multiple target sequences without mutual interference. The benefit of competitive binding of labeled quenched Oligo 1/2 forward primers with unlabeled Oligo 3 (see FIG. 1(a)) is demonstrated as a means to optimize signal within a reduced time range for the amplification reaction. Similar benefits are contemplated with backward primers (for example in LAMP) using labeled, quenched Oligo 5/6 with unlabeled Oligo 4 (see FIG. 1(b) (ii)).

Figure 1:
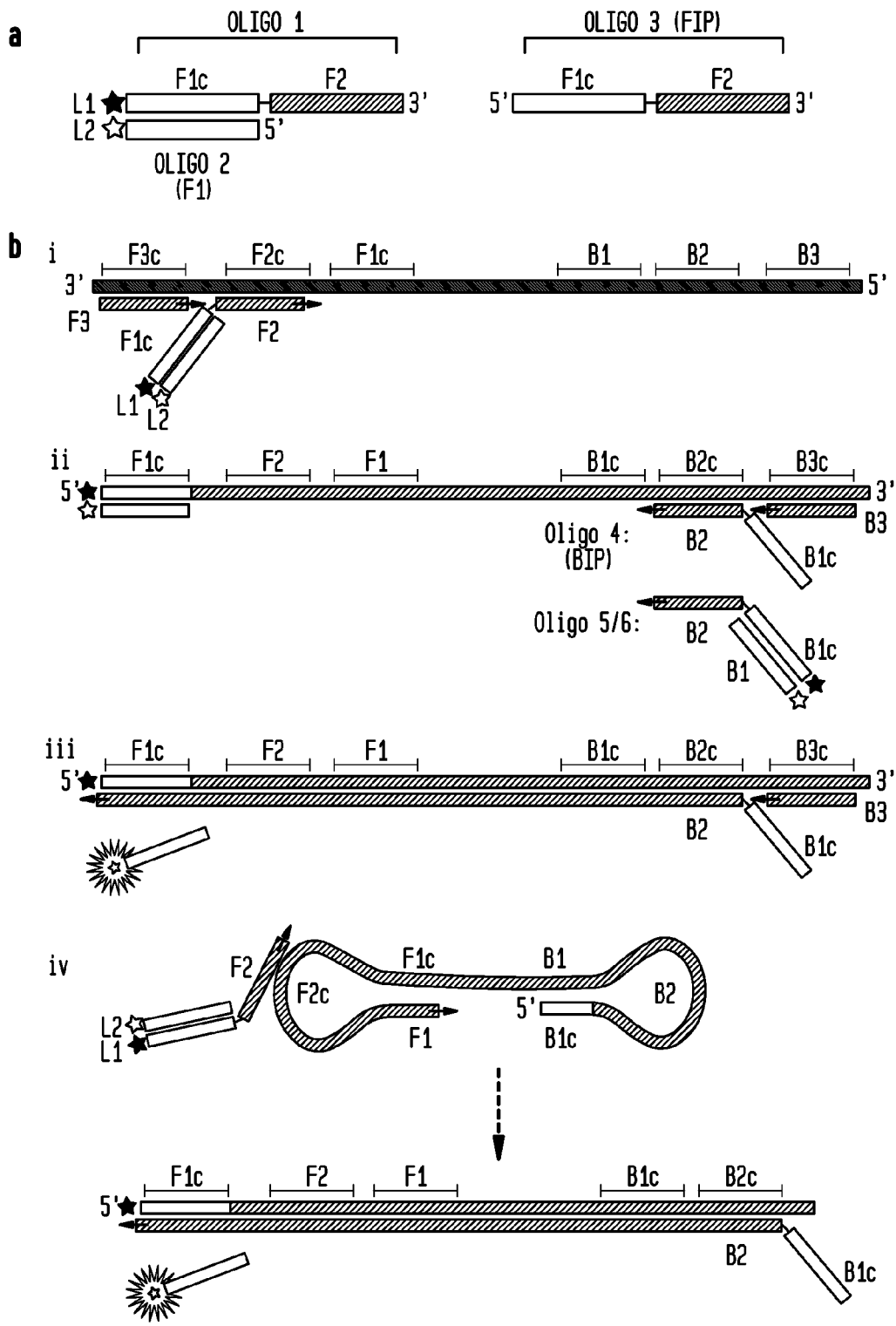
FIGS. 1(a) and 1(b) schematically shows LAMP amplification using labeled oligonucleotides and non-labeled oligonucleotides for forward and backward strand displacement. The abbreviations used are as follows: "F"=forward, "B"=backward, "FIP"=forward interior primer, "C"=complementary. The LAMP reaction relies on a strand-displacing polymerase.
Figure 2:
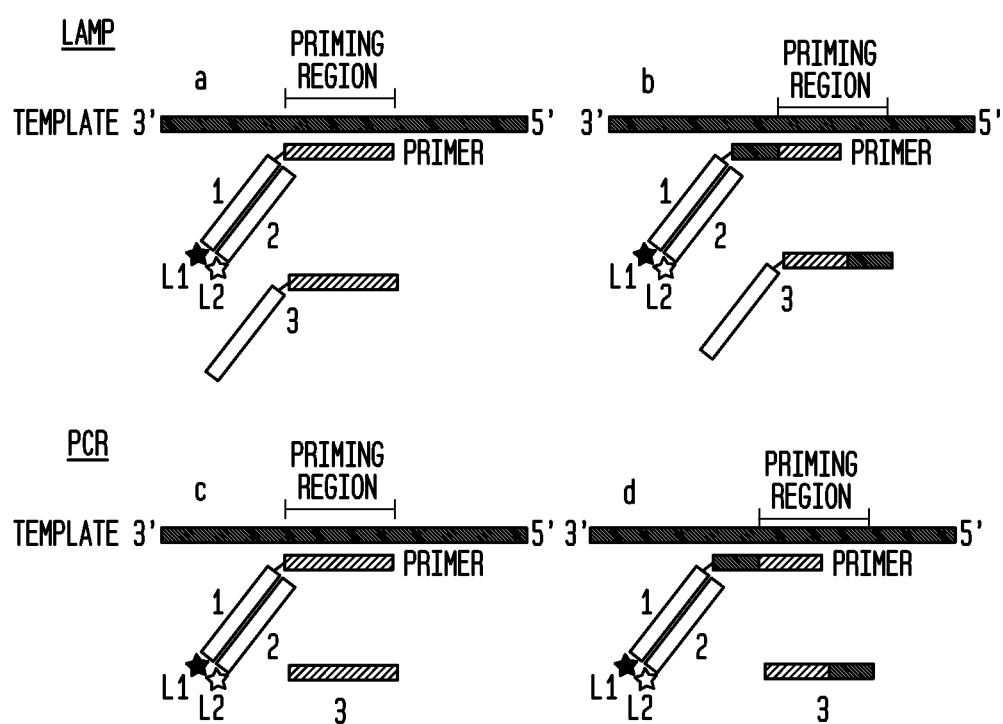
FIG. 2(a)-(d) shows primer designs for LAMP and PCR amplification using labeled Oligo 1/2 and unlabeled Oligo 3 as defined in FIG. 1(a) at the 5' end of the template polynucleotide. Primer sequence complementary to the target polynucleotide is found in both Oligo 1 and 3 (F2).

The set of probes described herein for use in isothermal and PCR amplification methods utilize a sequence modified either at the 5' end or internally with either a dark quencher or a fluorophore. For probe creation, a complementary oligonucleotide modified either at the 3' or internally with either a dark quencher or a fluorophore spectrally overlapping with the fluorophore or dark quencher of the complementary region is annealed to part of a larger single stranded polynucleotide. This creates a duplex region while leaving a single strand 3' "flap" for annealing to target nucleic acid (Oligo 2; FIG. 1(a)). The labels do not negatively affect the sensitivity of the amplification reaction, but the duplex region confers a delay in detection threshold time, mitigated by competitive binding between labeled quenched Oligo 1/2 and unmodified Oligo 3 (FIG. 2(a)-(d), FIG. 5). Although the present embodiments are broadly applicable to a wide range of amplification techniques, for example SDA, HDA, nicking enzyme amplification reaction (NEAR), recombinase polymerase amplification (RPA), ICAN, multiple displacement amplification (MDA), multiply primed rolling circle amplification (MPRCA), nucleic acid sequence-based amplification (NASBA), self-sustained sequence replication (3SR), smart amplification process (SmartAmp), ramification amplication (RAM), and genome exponential amplification reaction (GEAR), LAMP and PCR are discussed below in more detail. These examples however are not intended to be limiting.

In primer design for LAMP, the F1c regions may be 15-50 bases, for example 20-25 bases and can be designed to feature a $T_m$ from 50° C.-80° C. Thus, the Oligo 1:Oligo 2 duplex is optionally designed to be stably annealed at 63° C.-65° C. (suitable for LAMP) and no signal is observed in the absence of strand-displacing DNA polymerase. However, if shorter primer sequences with lower melting temperature are required, for example, a specific $T_m$ is required for SNP or methylation detection, or for short regions due to weakly conserved targets, reactions can be performed at lower temperatures to accommodate less stable duplexes. The F1c primer sequences provided in Table 1 range in $T_m$ from 61° C.-74° C. and all perform LAMP reactions at 60° C.-65° C., showing that use of F1c:Fd duplexes does not limit primer design considerations. A primer pair was also tested as described above with fluorophore and quencher positions switched on Oligo 1 (here, fluorophore) and 2 (dark quencher). Use of this reverse orientation primer set (λ) resulted in similar amplification detection efficiency (FIG. 3(a)-(b) FIG. 4(a)-(b)).

Figure 5:
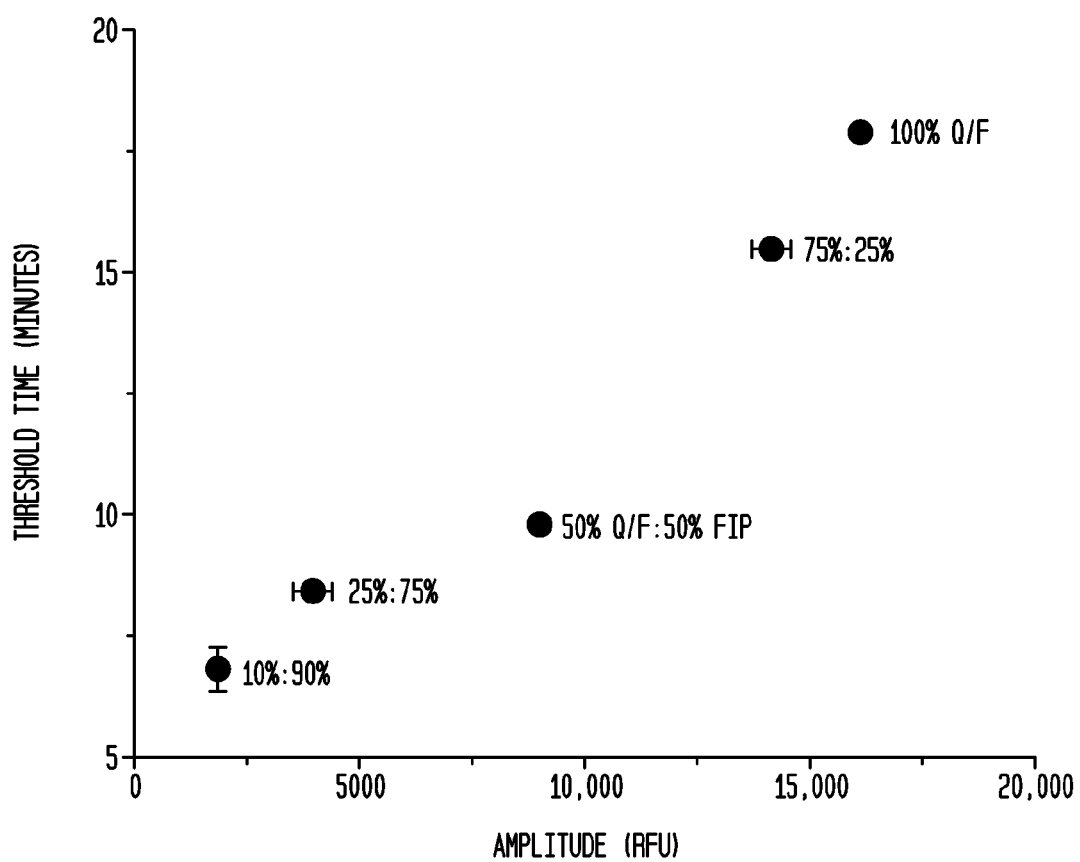
FIG. 5 shows effects of the stoichiometry of Oligos 1/2 and 3 on both amplification threshold time and signal amplitude in LAMP reactions performed with dnaE/Cy5 and 5 ng E. coli genomic DNA. The X-axis is background-subtracted Cy5 signal from displacement of Oligo 2 and the y-axis is threshold time ($C_t$) of each reaction. Use of 100% Oligo 1/2 or 75% Oligo 1/2:25% Oligo 3 resulted in high signal amplitude, but substantially increased threshold time. Use of 25% Oligo 1/2:75% Oligo 3, or 10% Oligo 1/2:90% Oligo 3 provided fast amplification detection times, but significantly decreased fluorescence signal. Use of 50% Oligo 1/2:50% Oligo 3 provided a balance of fast amplification with high signal amplitude.

The inclusion of an Oligo 3 which shares the same sequence as Oligo 1 maintains the speed and amplification detection threshold of unlabeled reactions, reducing any inhibition from duplex and labeled primers (FIG. 5).

In primer design for PCR, standard protocols in the art are used for design of the forward (F) and reverse (R) primer. This involves selecting a sequence having similar $T_m$, and moderate G/C content. The duplex region formed from Oligo 1 and Oligo 2 is designed with sufficient $T_m$ to remain annealed as duplex DNA during the amplification reaction ($T_m$ oligo $2 > T_A$). These parameters may be varied according to G/C content for example Oligo 2 is 48.8% G/C and has a $T_m$ of 66° C. The primer may include an Oligo 2 having a length of at least 30 bases, and a $T_m$ greater than the annealing temperature and greater than or similar to the extension temperature (here 61° C. and 68° C., respectively). Other lengths of duplex region can be used, with the only requirement being to perform PCR reactions with extension temperatures near or below the $T_m$ of oligonucleotide 2; for example if $T_m$ of oligonucleotide is 61° C., an extension temperature of 50° C.-62° C. provides sufficient annealing efficiency. High affinity between Oligo 1 and Oligo 2 avoids false positives that might otherwise occur due to spurious primer annealing. A fluorescent signal is observed when F2 is displaced using a probe by amplifying DNA polymerase activity.

The detection primer (Oligo 1) is determined by synthesis of the F and B primer with additional sequence 5' of the primer. The complement of this additional sequence region (Oligo 2) is annealed to form the detection primer duplex. The duplex is formed from equimolar amounts of Oligo 1 and Oligo 2 that are preformed prior to being combined with Oligo 3 in the reaction mixture.

The inclusion of a truncated Oligo 3 in the PCR reaction maintains the speed and amplification detection threshold of unlabeled reactions, reducing any inhibition from duplex and labeled primers (FIG. 5).

Examples of fluorescence labels for use in this method includes fluorescein, 6-FAM™ (Applied Biosystems, Carlsbad, Calif.), TET™ (Applied Biosystems, Carlsbad, Calif.), VIC™ (Applied Biosystems, Carlsbad, Calif.), MAX, HEX™ (Applied Biosystems, Carlsbad, Calif.), TYE™ (ThermoFisher Scientific, Waltham, Mass.), TYE665, TYE705, TEX, JOE, Cy™ (Amersham Biosciences, Piscataway, N.J.) dyes (Cy2, Cy3, Cy3B, Cy3.5, Cy5, Cy5.5, Cy7), Texas Red® (Molecular Probes, Inc., Eugene, Oreg.), Texas Red-X, AlexaFluor® (Molecular Probes, Inc., Eugene, Oreg.) dyes (AlexaFluor 350, AlexaFluor 405, AlexaFluor 430, AlexaFluor 488, AlexaFluor 500, AlexaFluor 532, AlexaFluor 546, AlexaFluor 568, AlexaFluor 594, AlexaFluor 610, AlexaFluor 633, AlexaFluor 647, AlexaFluor 660, AlexaFluor 680, AlexaFluor 700, AlexaFluor 750), DyLight™ (ThermoFisher Scientific, Waltham, Mass.) dyes (DyLight 350, DyLight 405, DyLight 488, DyLight 549, DyLight 594, DyLight 633, DyLight 649, DyLight 755), ATTO™ (ATTO-TEC GmbH, Siegen, Germany) dyes (ATTO 390, ATTO 425, ATTO 465, ATTO 488, ATTO 495, ATTO 520, ATTO 532, ATTO 550, ATTO 565, ATTO Rho101, ATTO 590, ATTO 594, ATTO 610, ATTO 620, ATTO 633, ATTO 635, ATTO 637, ATTO 647, ATTO 647N, ATTO 655, ATTO 665, ATTO 680, ATTO 700, ATTO 725, ATTO 740), BODIPY® (Molecular Probes, Inc., Eugene, Oreg.) dyes (BODIPY FL, BODIPY R6G, BODIPY TMR, BOPDIPY 530/550, BODIPY 558/568, BODIPY 564/570, BODIPY 576/589, BODIPY 581/591, BODIPY 630/650, BODIPY 650/665), HiLyte Fluor™ (AnaSpec, Fremont, Calif.) dyes (HiLyte Fluor 488, HiLyte Fluor 555, HiLyte Fluor 594, HiLyte Fluor 647, HiLyte Fluor 680, HiLyte Fluor 750), AMCA, AMCA-S, Cascade® Blue (Molecular Probes, Inc., Eugene, Oreg.), Cascade Yellow, Coumarin, Hydroxycoumarin, Rhodamine Green™-X (Molecular Probes, Inc., Eugene, Oreg.), Rhodamine Red™-X (Molecular Probes, Inc., Eugene, Oreg.), Rhodamine 6G, TMR, TAMRA™ (Applied Biosystems, Carlsbad, Calif.), 5-TAMRA, ROX™ (Applied Biosystems, Carlsbad, Calif.), Oregon Green® (Life Technologies, Grand Island, N.Y.), Oregon Green 500, IRDye® 700 (Li-Cor Biosciences, Lincoln, Nebr.), IRDye 800, WellRED D2, WellRED D3, WellRED D4, and Lightcycler® 640 (Roche Diagnostics GmbH, Mannheim, Germany).

Suitable quenchers include Black Hole Quencher®-1 (Biosearch Technologies, Novato, Calif.), BHQ-2, Dabcyl, Iowa Black® FQ (Integrated DNA Technologies, Coralville, Iowa), IowaBlack RQ, QXL™ (AnaSpec, Fremont, Calif.), QSY 7, QSY 9, QSY 21, QSY 35, and IRDye QC.

Bright fluorophores with extinction coefficients >50,000 $M^{-1} cm^{-1}$ and appropriate spectral matching with the fluorescence detection channels can be used to overcome loss of fluorescence signal due to dilution of template-specific Oligo 2 in multiplex reactions.

In one embodiment, ROX™ (Integrated DNA Technologies, Coralville, Iowa) was found to be extremely effective (>20,000 background-subtracted fluorescence counts in single-plex reactions), using the 15 nm wider detection channel (Channel 3, CFX96™, Bio-Rad, Hercules, Calif.). Cy5, Cy5.5, and HEX gave similarly high signal (10,000-15,000).

The number of different samples in a single reaction vessel and their detection is limited only by access to different fluorescent markers and to a fluorimeter with multiple channels (CFX96 as shown, 5 channels) or by the limitations of capillary electrophoresis. The method described herein is amenable to high-plex amplification, such as might be achieved using fluorimeters such as the ICEPlex® (PrimeraDx, Mansfield, Mass.), which can detect 60 targets using fluorescence and capillary electrophoresis, and xMAP® (Luminex, Austin, Tex.), which can identify 500 targets.

The choice of a polymerase for use in a quantitative amplification reaction using polymerase dependent extension and displacement can modulate detection threshold. For example, LAMP utilizes a strand displacing DNA polymerase (for example, Bst DNA polymerase, large fragment) for detection through strand displacement, having an activity at elevated temperatures of, for example, 50° C.-70° C. and being stable at that temperature for >30 minutes.

Variants of existing polymerases can be readily screened by performing a standard LAMP assay. One example assay is a standard LAMP using lambda DNA (Nagamine, et al. (2002)), in which sufficient amplification of 5 ng lambda phage genomic DNA is considered to be threshold detection in less than 30 minutes at 60° C.-68° C. using standard primer concentrations.

In one embodiment, the results showed that amplification efficiencies in single or multiplex reactions could be further enhanced by selecting polymerases. For example, LAMP reactions could be enhanced by using polymerase variants such as Bst 2.0 or Bst 2.0 WarmStart™ DNA polymerases (New England Biolabs, Ipswich, Mass.), compared with wild-type Bst DNA polymerase, large fragment where the multiplex reaction time could be reduced to as little as 5-30 minutes without significant reduction in signal.

In another example, PCR reactions containing strand-displacing 9° N™ polymerase (New England Biolabs, Ipswich, Mass.) or a blend of a strand displacement polymerase and Taq (see for example, OneTaq, New England Biolabs, Ipswich, Mass.) provided much more robust signal than those with Taq alone, indicating without wishing to be limited by theory, that an increased efficiency of separating Oligo 2 and Oligo 1 might occur due to strand-displacement activity compared to 5'-3' exonuclease activity alone. Strand-displacing DNA polymerase is included at a 0.01-0.5 ratio relative to Taq or non-strand-displacing polymerase.

Standard PCR polymerases that contain 5'-3' exonuclease activity (e.g. Taq DNA polymerase and variants) or strand displacement activity (e.g. 9° N, Vent™ DNA polymerase (New England Biolabs, Inc., Ipswich, Mass.)) are suitable for use in the PCR embodiments as either activity will generate signal by separating the quencher/fluorophore duplex of Oligo 1/2.

Multiplexing of samples and detection of amplification products can be achieved in a single reaction vessel as described herein.

The Figures and Examples while not intended to be limiting show that amplification products from multiple target sequences can be detected in a single amplification reaction tube (see for example, FIGS. 3(a)-(b) and 4(a)-(b)). A dynamic range for isothermal or PCR amplification methods for single and multiplex reactions maintains a detection sensitivity in the range of at least $5-10^9$ copies of polynucleotide template with an ability to accurately detect below 1000 copies, 500 copies, 100 copies, or as few as 50 copies, 10 copies or 5 copies of a target sequence.

The reaction pathway for polymerase dependent extension reactions shown in FIG. 1(b)(i-iv) can be extended to (n) target reactions where total primer concentration may be maintained at a constant concentration, equivalent to the amount optimized in the singleplex reaction. Each template-specific primer set concentration may be adjusted for the number of targets (n) in a multiplex reaction with each primer set being 1/n. An internal control can be included for purposes of quantitation of the target polynucleotide (see for example, FIG. 3(c)). In the examples, robust amplification in a multiplex environment is shown for two (FIG. 3(a)-(c)), three (FIG. 4(a)) or four (FIG. 4(b)) targets.

Multiplexed amplification reactions for isothermal and PCR amplification can maintain a level of independent performance, with each simultaneous amplification retaining sensitivity to low copy numbers and providing robust amplification. This property enabled the quantitative measurement of a test target nucleic acid sample while simultaneously measuring a positive control sample, as shown for example, in FIG. 3(c) for LAMP. This ability to perform internal control reactions is an important diagnostic feature enabled by the described methodology.

Figure 7:
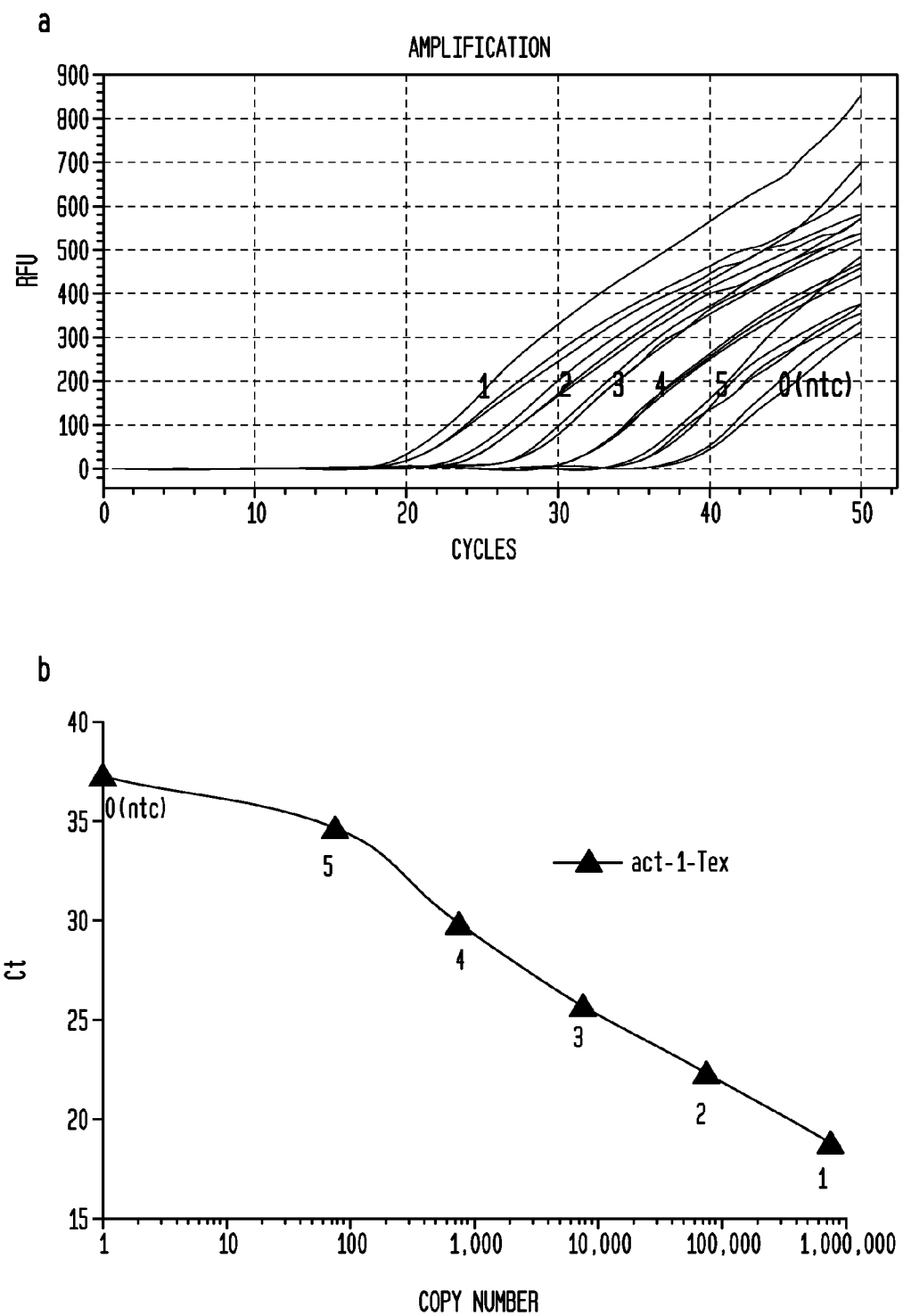
FIG. 7(a)-(c) shows that both copy number and size determinations for C. elegans act-1 gene can be determined using a 10-fold dilution series of genomic DNA (approximately 760000 to 76 copies, labeled 1-5) and a non-template control reaction (ntc).

Size determination can be performed by means of downstream analysis including capillary electrophoresis, which separates products based on size and can detect fluorescent labels. Products from single or multiplex reactions containing fluorophore-labeled Oligo 1 can be further analyzed to determine size of product and specificity of reaction (FIG. 7(a)-(c)). This also greatly increases the degree of multiplexing, as multiple product sizes with the same fluorescent label can be distinguished by electrophoretic separation.

All references cited herein are incorporated by reference.

EXAMPLES

Example 1

Multiple Target Detection Using Isothermal Amplification

Components of a LAMP reaction include:
(a) Primers for LAMP
These were designed either manually or using Primer Explorer V4 (Eiken Chemical, Tokyo, Japan). Sequences can be found in Table 1, and all synthetic oligonucleotide primers, Q-FIP/oligonucleotide 1, and Fd/Oligo 3 were synthesized by Integrated DNA Technologies (Coralville, Iowa). The dark quencher was either Iowa Black FQ or RQ, and fluorophores used were 6-FAM, HEX, ROX, Cy5, and Cy5.5, each corresponding to one of 5 channels in a CFX96 Real Time System, used for performing LAMP reactions were also obtained from Integrated DNA Technologies.

(b) Target DNA:
Lambda phage genomic DNA (5 ng per reaction) and HeLa genomic DNA (100 ng per reaction) were from New England Biolabs, Inc. (Ipswich, Mass.).

E. coli genomic DNA (5 ng per reaction) was from Affymetrix (Santa Clara, Calif.) and C. elegans genomic DNA (82.5 ng per reaction) was purified using standard procedures.

(c) Oligo 1/2 duplexes were annealed by heating 50 µM Q-FIP and 50 µM Fd to 98° C. and slowly cooling mixture to room temperature.

(d) LAMP reactions with Bst 2.0 DNA polymerase or Bst 2.0 WarmStart DNA polymerase were performed in 1× Isothermal Amplification Buffer (New England Biolabs, Ipswich, Mass.): 20 mM Tris-HCl (pH 8.8, 25° C.), 10 mM $(NH_4)_2SO_4$, 50 mM KCl, 2 mM $MgSO_4$, 0.1% Tween® 20 (Sigma-Aldrich, St. Louis, Mo.) supplemented to 8 mM $MgSO_4$ and 1.4 mM each of dATP, dCTP, dGTP, and dTTP.

Each reaction included the following components: 1.6 µM FIP (or 0.8 µM FIP Oligo 3 and 0.8 µM Q-FIP:Fd Oligo 1:Oligo 2), 1.6 µM BIP, 0.2 µM F3 and B3, 0.4 µM LoopF and LoopB, in addition to 0.64 U/µL Bst DNA polymerase, LF, Bst 2.0 DNA polymerase, or Bst 2.0 WarmStart DNA polymerase.

Multiplexing Using LAMP Using Oligonucleotides 1-3 and 5 Additional Primer Oligonucleotides To test the method schematically laid out in FIGS. 1(a) and (b)(i-iv) for LAMP detection of four target DNAs, four sets of LAMP primers with oligonucleotide and accompanying oligonucleotide 2 probes were designed, each with a different fluorophore and quencher pair. Targeted genes from different organisms and genome complexities: E. coli dnaE (Iowa Black RQ/Cy5); C. elegans lec-10 (RQ/ROX); human Cystic Fibrosis Transmembrane Conductance Regulator (CFTR; FQ/6-FAM); and human BRCA1 (RQ/Cy5.5) were analyzed. Additionally, a set of LAMP primers were adapted for bacteriophage A DNA (Nagamine, et al. (2002)) with the quencher and fluorophore positions reversed (5'-HEX Oligo 1/3'-FQ Oligo 2) to examine any effect of quencher/fluorophore location. Oligo 1/2 were made for each primer set, and LAMP reactions performed using Oligo 1/2 and Oligo 3.

Total oligonucleotide concentrations were kept to those described for a standard LAMP reaction (total primer concentration was kept to 5.2 µM regardless of the number of templates, with each primer set adjusted by 1/n where n is number of targets in the reaction in multiplex reactions; Table 3).

Reactions were performed at 65° C. in triplicate, and all presented $C_t$ values represent an average±standard deviation.

Figure 3:
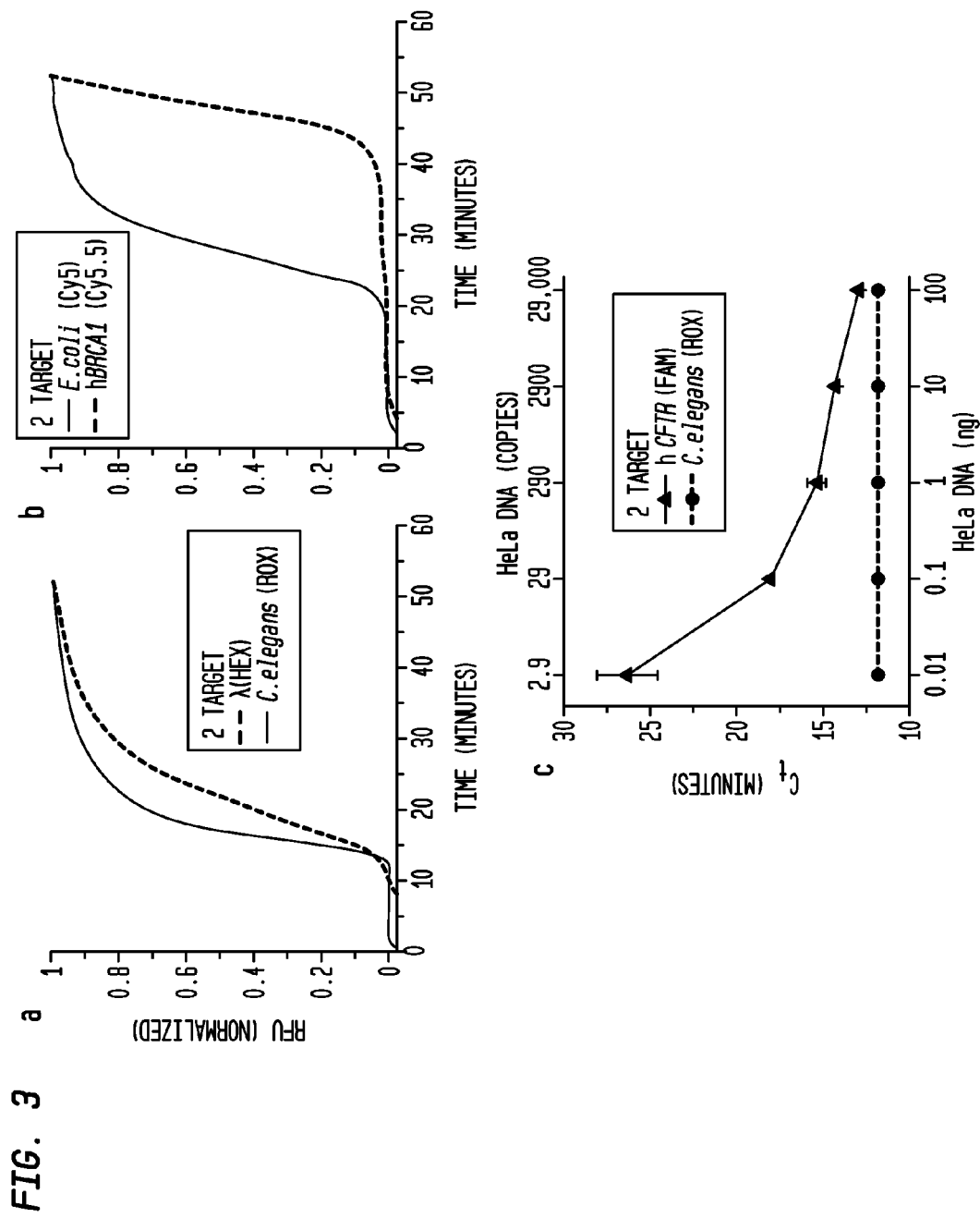
FIG. 3(a)-(c) shows that the amplification methods shown in FIGS. 1(b)(i-iv) and FIG. 2(a)-(b) can be used effectively in multiplex LAMP reactions even if the amplification rate varies for different polynucleotides having different fluorescent labels. Relative fluorescent units normalized to maximum fluorescence (RFU) is plotted against time of the reaction (minutes). For the duplex reactions shown in FIG. 3(a)-(c), primer concentration was scaled by ½ for each primer set as compared to single-plex reactions. Reactions contained eight oligonucleotides per target and sixteen total oligonucleotides in duplex reaction.

Results from duplex reactions are shown in FIG. 3(a)-(c). Fluorescence curves from LAMP reactions result from two distinct, complete oligonucleotide sets and their corresponding genomic DNA targets. Distinct targets were detected in a single LAMP reaction. Curves shown are normalized to maximum fluorescence signal in that channel to account for differences in the signal intensity of various fluorophores. The detection provided a robust signal for each target regardless of the speed of their independent amplification, which varies according to the nature of the primers, templates, and target copy number. Some amplification reactions reached exponential phase more rapidly than others. The amplification reactions with a higher $C_t$ were not affected by the faster amplification reactions in the same tube, obviating the need for consideration of amplification speed in multiplex reactions (FIG. 3(a)-(b), 4(a)-(b)).

Because the amplification reactions in the same reaction vessel are independent of each other, sensitivity can be maintained for each sample in the mixture (FIG. 3(c)). FIG. 3(c) shows that FAM-CFTR is detected to ~2.9 copies of HeLa genomic DNA (10 pg) in a single reaction consistent with robust LAMP for ROX-lec-10 (82.5 ng C. elegans DNA, ~7.6×10$^5$ copies). Thus a robust LAMP standard curve can be generated across a copy number range of Target 1 (here, CFTR) while Target 2 (lec-10) is detected simultaneously. Amplification of the constant target remains unchanged (all 5 ROX $C_t$ values 11.8±0.03 minutes) across the copy number range of the variable target providing a reliable positive control (FIG. 3(c)). This property allows LAMP to be performed with an internal standard, an important consideration for diagnostic applications. FIG. 3(c) demonstrates performance at low copy numbers, but high copy numbers are also reliably detected as shown in FIG. 3(a) (5 ng λ DNA, ~10$^8$ copies) and FIG. 3(b) (5 ng E. coli genomic DNA, ~10$^6$ copies).

Use of the present detection method thus imposed no limitation to the sensitivity of the LAMP reaction. Similarly, the dynamic range of LAMP is unaffected by the detection methodology described herein in a duplex reaction, which maintained robust detection from 10-10$^8$ copies.

Figure 4:
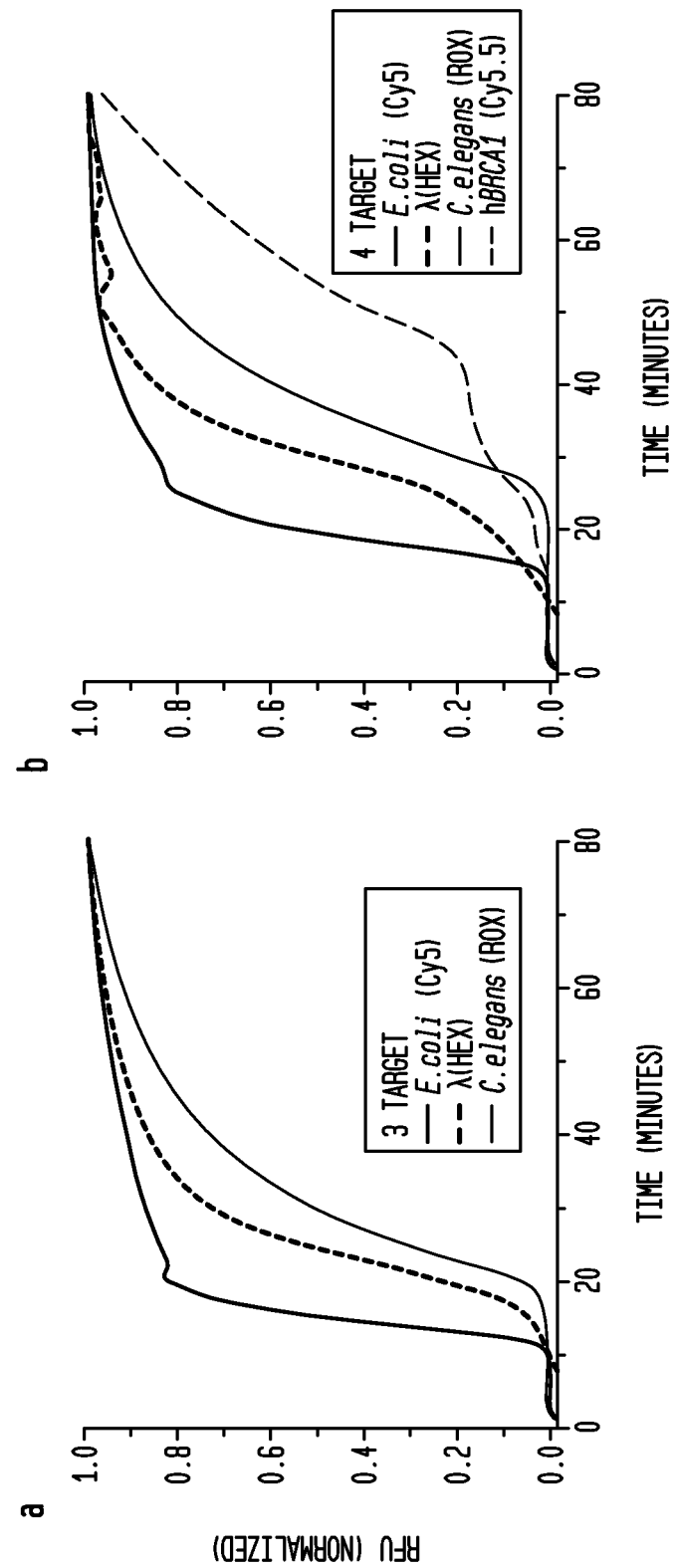
FIG. 4(a)-(b) show single multiplex reactions consisting of 3 and 4 targets where the number of detection reactions in a multiplex reaction is limited only by the availability of distinguishable fluorescent tags and the number of channels in a fluorimenter or capillary electrophoresis device.

The detection methodology described herein can readily be extended to three and four target reactions (FIG. 4(a)-(b)), again with total primer concentration constant and each set adjusted for number of targets. Reducing primer concentration three- or four-fold does accordingly increase time to reach threshold. This drop in time was consistent, making template quantification reliable, and the reaction times were still rapid with Bst 2.0 DNA polymerase. The multiplexed reactions displayed robust amplification of three (FIG. 4(a)) or four (FIG. 4(b)) targets, with loss of signal amplitude accompanying decreased concentration of the fluorophore-containing primer.

Example 2

PCR Using Oligo 1, 2 and 3 and a Fourth Oligonucleotide as a Second Primer

Realtime PCR was performed to detect the E. coli 16s rRNA gene. The primers (Table 2) contained regular PCR primers (F, Oligo 3, and R primers) at 200 µM each and a pair of detection primers (Oligo 1, and Oligo 2) at 80 µM each (schematic in FIG. 2(c)).

PCR reactions were performed with Taq DNA polymerse and strand-displacing 9° N DNA polymerase using ten-fold serial dilutions of E. coli genomic DNA from 100 ng to 0.1 pg (equivalent of 20×10$^6$ to 20 copies) using 1× Standard Taq buffer supplemented with MgCl$_2$ to a final 2.25 mM, 400 µM of each of the four dNTPs in 25 µl reaction volume, 1.25 U Taq DNA polymerase, and 0.05 U 9° N$_m$ DNA polymerase.

Figure 6:
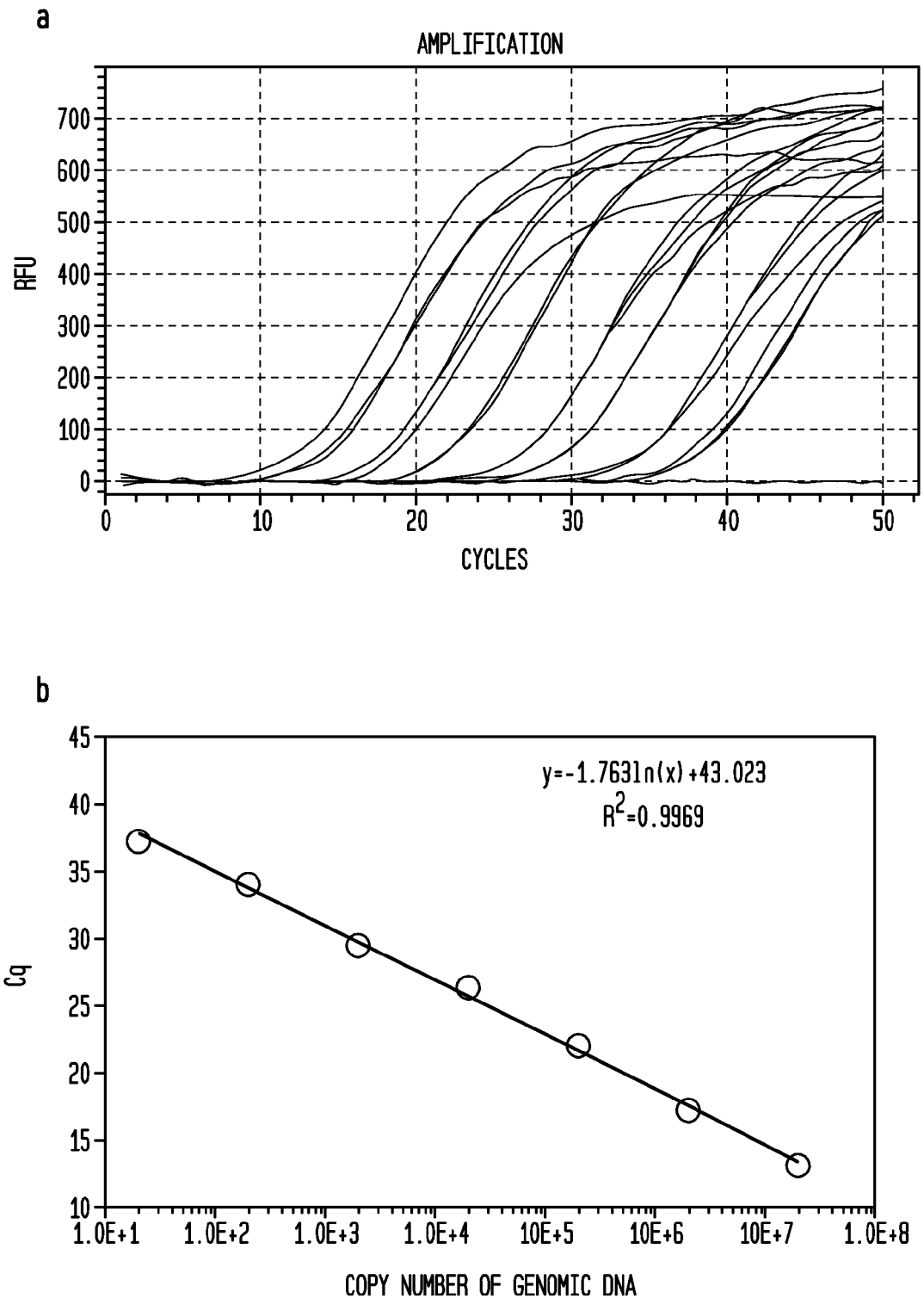
FIG. 6(a)-(b) shows detection of PCR amplification using Oligos 1/2 and Oligo 3. Realtime PCR was performed to detect the E. coli 16s rRNA gene. The primers (FIG. 2, Table 2) contain regular PCR primers (F, Oligo 3, and R primers) at 200 µM each and a pair of primers (D-F, Oligo 1, and Fq, Oligo 2) at 80 uM each. Ten-fold serial dilutions of E. coli genomic DNA from 100 ng to 0.1 pg (equivalent of $20 \times 10^6$ to 20 copies) were used as template.

The PCR cycle and realtime signal acquisition was performed on a CFX96 machine with cycle condition at 95° C. for 2 minutes; 50 cycles at 95° C. for 10 seconds, 61° C. for 15 seconds and 68° C. for 30 seconds; final incubation at 68° C. for 5 minutes. The cycle number at signal that crosses the amplification threshold (Cq value, Y axis) was plotted against the log value of the copy number. As shown, the resulting qPCR data was robust and sensitive to low copy number, providing a high-$R^2$ (0.9969). The results are shown in FIG. 6(a)-(b).

Size Determination of Polynucleotides after qPCR

An advantage of the above qPCR methodology over other conventional qPCR techniques is that the fluorescent label on the reporter primer is incorporated into the PCR product and can be visualized directly on instruments such as capillary electrophoresis (CE). As an example, a qPCR was performed to detect C. elegans act-1 gene using approximately 760,000 to 76 copies of genomic DNA in a 10-fold dilution series. The act-1 reporter probe was labeled with Tex fluorescence dye and the signal was acquired using CFX96 qPCR machine. The PCR cycle condition was: 95° C. for 1 minute, then 50 cycles of 95° C. for 10 seconds, 61° C. for 15 seconds and 68° C. for 30 seconds. As expected, the Ct value correlated tightly with the copy number of the target gene in the DNA quantification curve (FIGS. 7(a) and 7(b)). After completion of the PCR cycling, the product was diluted 20-fold with water and subjected to size analysis using ABI 3130 CE instrument. The expected size of the PCR product (154 bp) was detected in all PCR reactions containing the template DNA from 760,000 to 76 copies (FIG. 7(c)), while in the reaction containing no template DNA there was no specific peak. This additional step provides further confirmation of the PCR product and thus increases the confidence of target identification. As both PCR and CE analysis can be automated and the combination of them would allow the high accuracy detection of large scale samples such as in patient genotyping analysis or pathogen detection.

TABLE 1

LAMP Oligonucleotide Sequences
LAMP Primer Sequences

E. coli dnaE

Q-FIP (1) 5'-IAbRQ-
CTGCCCCGACGATAGGCTTAATCGTGGTCTGGTGAAGTTCTACGG
(SEQ ID NO: 1)

TABLE 1-continued

LAMP Oligonucleotide Sequences
LAMP Primer Sequences

| | |
|---|---|
| Fd (2) | ATTAAGCCTATCGTCGGGGCAG-Cy5-3' (SEQ ID NO: 2)<br>(Tm = 67.8° C.) |
| FIP | CTGCCCCGACGATAGGCTTAATCGTGGTCTGGTGAAGTTCTACGG<br>(SEQ ID NO: 3) |
| BIP | TCCAGTGCGACCTGCTGGGTGGGTATTGTTCGCCGCCAGTAC<br>(SEQ ID NO: 4) |
| F3 | GATCACCGATTTCACCAACC (SEQ ID NO: 5) |
| B3 | CTTTTGAGATCAGCAACGTCAG (SEQ ID NO: 6) |
| LoopF | TGCGCCATGTCCCGCT (SEQ ID NO: 7) |
| LoopB | TGAGTTAACCCACCTGACG (SEQ ID NO: 8) | lambda

| | |
|---|---|
| Q-FIP (1) | 5'-HEX-<br>CAGCCAGCCGCAGCACGTTCGCTCATAGGAGATATGGTAGAGCCGC<br>(SEQ ID NO: 9) |
| Fd (2) | CGAACGTGCTGCGGCTGGCTG-IABkFQ-3' (SEQ ID NO: 10)<br>(Tm = 73.8° C.) |
| FIP (3) | CAGCCAGCCGCAGCACGTTCGCTCATAGGAGATATGGTAGAGCCGC<br>(SEQ ID NO: 11) |
| BIP | GAGAGAATTTGTACCACCTCCCACCGGGCACATAGCAGTCCTAGGGACAG<br>T(SEQ ID NO: 12) |
| F3 | GGCTTGGCTCTGCTAACACGTT (SEQ ID NO: 13) |
| B3 | GGACGTTTGTAATGTCCGCTCC (SEQ ID NO: 14) |
| LoopF | CTGCATACGACGTGTCT (SEQ ID NO: 15) |
| LoopB | ACCATCTATGACTGTACGCC (SEQ ID NO: 16) |

C.elegans lec-10

| | |
|---|---|
| Q-FIP (1) | 5'-IAbRQ-GATTCCACTTCCAACGTCGTTGCATAGGCATTGTATCCAGAGTG<br>(SEQ ID NO: 17) |
| Fd (2) | CAACGACGTTGGAAGTGGAATC-Rox_N-3' (SEQ ID NO: 18)<br>(Tm = 65.5° C.) |
| FIP (3) | GATTCCACTTCCAACGTCGTTGCATAGGCATTGTATCCAGAGTG<br>(SEQ ID NO: 19) |
| BIP | CGAAGTGAACCTTGTCAACATGAGACTACCCACATCGTTACC<br>(SEQ ID NO: 20) |
| F3 | AGCAACATAGGTTTCAGTTC (SEQ ID NO: 21) |
| B3 | CTGTGAACGGTCATCACC (SEQ ID NO: 22) |
| LoopF | ACGGACATGTCGATCATGGA (SEQ ID NO: 23) |
| LoopB | CGTCTCCCTTCAATCCGATGGC (SEQ ID NO: 24) |

Human CFTR

| | |
|---|---|
| Q-FIP (1) | 5'-IAbFQ-<br>CCAAAGAGTAAAGTCCTTCTCTCTCGAGAGACTGTTGGCCCTTGAAGG<br>(SEQ ID NO: 25) |
| Fd (2) | AGAGAGAAGGACTTTACTCTTT-6-FAM-3' (SEQ ID NO: 26)<br>(Tm = 60.7° C.) |
| FIP (3) | CCAAAGAGTAAAGTCCTTCTCTCTCGAGAGACTGTTGGCCCTTGAAGG<br>(SEQ ID NO: 27) |
| BIP | GTGTTGATGTTATCCACCTTTTGTGGACTAGGAAAACAGATCAATAG<br>(SEQ ID NO: 28) |

TABLE 1-continued

LAMP Oligonucleotide Sequences
LAMP Primer Sequences

| | |
|---|---|
| F3 | TAATCCTGGAACTCCGGTGC (SEQ ID NO: 29) |
| B3 | TTTATGCCAATTAACATTTTGAC (SEQ ID NO: 30) |
| LoopF | ATCCACAGGGAGGAGCTCT (SEQ ID NO: 31) |
| LoopB | CTCCACCTATAAAATCGGC (SEQ ID NO: 32) |

Human BRCA1

| | |
|---|---|
| Q-FIP (1) | 5'-IAbRQ-ATCCCCAGTCTGTGAAATTGGGCAAAATGCTGGGATTATAGATGT (SEQ ID NO: 33) |
| Fd (2) | CCAATTTCACAGACTGGGGAT-Cy5.5Sp-3' (SEQ ID NO: 34) (Tm = 64.4° C.) |
| FIP (3) | ATCCCCAGTCTGTGAAATTGGGCAAAATGCTGGGATTATAGATGT (SEQ ID NO: 35) |
| BIP | GCAGCAGAAAGATTATTAACTTGGG-CAGTTGGTAAGTAAATGGAAGA (SEQ ID NO: 36) |
| F3 | TCCTTGAACTTTGGTCTCC (SEQ ID NO: 37) |
| B3 | CAGTTCATAAAGGAATTGATAGC (SEQ ID NO: 38) |
| LoopF | AGAACCAGAGGCCAGGCGAG (SEQ ID NO: 39) |
| LoopB | AGGCAGATAGGCTTAGACTCAA (SEQ ID NO: 40) |

TABLE 2

PCR Primer Sequences

E. coli 16s rRNA

| | |
|---|---|
| DF (1) | 5'-6-FAM-CCGCGTGTATGAAGAAGGCCTTCGGGTTGTAAAGTACTTTCAGCGGGGAGGAAGGGAGTAAAGTT (SEQ ID NO: 41) |
| Fq (2) | GAAAGTACTTTACAACCCGAAGGCCTTCTTCATACACGCGG-BHQ1-3' (SEQ ID NO: 42) |
| F (3) | AGCGGGGAGGAAGGGAGTAAAGTT (SEQ ID NO: 43) |
| R | CAGTATCAGATGCAGTTCCCAGGTT (SEQ ID NO: 44) |

C. elegans act-1

| | |
|---|---|
| DF (1) | 5'-TEX615-AGGATATGCCCTCCCACACGCCATCCTCCGTCTTGACTTGGCTGGACGTGATCTTACTGATTACC (SEQ ID NO: 45) |
| Fq (2) | CAAGTCAAGACGGAGGATGGCGTGTGGGAGGGCATATCCT-BHQ2-3' (SEQ ID NO: 46) |
| F (3) | GCTGGACGTGATCTTACTGATTACC (SEQ ID NO: 47) |
| R | GTAGCAGAGCTTCTCCTTGATGTC (SEQ ID NO: 48) |

TABLE 3

Oligonucleotide concentrations

| LAMP Primer | # Templates | | | | |
|---|---|---|---|---|---|
| | 1 | 2 | 3 | 4 | 5 |
| Q-FIP (1) | 800 nM | 400 | 267 | 200 | 160 |
| Fd (2) | 800 | 400 | 267 | 200 | 160 |
| FIP (3) | 800 | 400 | 267 | 200 | 160 |
| BIP | 1600 | 800 | 533 | 400 | 320 |
| F3 | 200 | 100 | 67 | 50 | 40 |
| B3 | 200 | 100 | 67 | 50 | 40 |
| LoopF | 400 | 200 | 133 | 100 | 80 |

The invention claimed is:

1. A method for detecting an amplification product of a polynucleotide, comprising:
  (a) amplifying a polynucleotide template in a reaction mix that comprises:
    (i) a first oligonucleotide for priming an amplification reaction, the first oligonucleotide comprising: i. a primer sequence that is complementary to a site in the template, ii. a tail sequence that is not complementary to the template and that is 5' of the primer sequence, and iii. a quencher or fluorescent label;
    (ii) a second oligonucleotide hybridized to the tail sequence of the first oligonucleotide to form a duplex, the second oligonucleotide having a fluorescent label if the first oligonucleotide has a quencher label, or having a quencher label if the first oligonucleotide has a fluorescent label;
    (iii) a third oligonucleotide comprising some or all of the primer sequence contained in the first oligonucleotide and not including a quenching or fluorescent label, wherein the third oligonucleotide is capable of hybridizing with the site in the template and with the second oligonucleotide;
    (iv) a strand-displacing polymerase; and
    (v) the polynucleotide template,
  (b) detecting the amplified product of the polynucleotide.

2. The method according to claim 1, wherein the polymerases is Bst polymerase, large subunit.

3. The method according to claim 1, wherein the reaction mix comprises a fourth oligonucleotide comprising a sequence for annealing to a priming site on a second location on the polynucleotide.

4. The method according to claim 1, wherein the reaction mix comprises a fourth, fifth and sixth oligonucleotide, wherein the fourth oligonucleotide is unlabeled and competes with a dimerized labeled fifth and sixth oligonucleotide.

5. The method according to claim 1, wherein the first oligonucleotide has a quencher label and the second oligonucleotide has a fluorescent label, or the first oligonucleotide has a fluorescent label and the second oligonucleotide has a quencher label.

6. The method according to claim 1, in the reaction mixture the ratio of the first oligonucleotide to the third oligonucleotide is in the range of 2:8 to 8:2.

7. The method according to claim 3, wherein the method comprises releasing the second oligonucleotide by extending the fourth oligonucleotide.

8. The method according to claim 1, wherein the amount of the first oligonucleotide is X/N where X is the primer concentration for optimal amplification of the product in a single-plex reaction and N is the number of different templates for which primer sets are present in the reaction mixture.

9. The method according to claim 8, wherein X is in the range of 0.1 μM-2 μM.

10. The method according to claim 1, wherein the amplifying is done by LAMP, or reverse transcription LAMP.

11. The method according to claim 1, wherein detecting an amplification product of a polynucleotide further comprises detecting an amplification product of multiple polynucleotides in a multiplex reaction mixture.

12. The method according to claim 11, wherein the multiplex reaction mixture contains an internal standard polynucleotide.

13. The method according to claim 1, further comprising determining the size of the amplification product.

14. The method according to claim 1, wherein the first oligonucleotide are present in the reaction mix at a molar ratio of at least a 1:1 ratio.

* * * * *